United States Patent
Ji

(10) Patent No.: US 10,398,531 B2
(45) Date of Patent: Sep. 3, 2019

(54) TRACTION BRACKET, ORTHODONTIC SYSTEM AND ORTHODONTIC METHOD THEREFOR

(71) Applicant: Li Ji, Guangdong (CN)

(72) Inventor: Li Ji, Guangdong (CN)

( * ) Notice: Subject to any disclaimer, the term of this patent is extended or adjusted under 35 U.S.C. 154(b) by 0 days.

(21) Appl. No.: 15/547,413

(22) PCT Filed: Jan. 26, 2016

(86) PCT No.: PCT/CN2016/072085
§ 371 (c)(1),
(2) Date: Oct. 25, 2017

(87) PCT Pub. No.: WO2016/119671
PCT Pub. Date: Aug. 4, 2016

(65) Prior Publication Data
US 2018/0055604 A1    Mar. 1, 2018

(30) Foreign Application Priority Data
Jan. 29, 2015 (CN) .......................... 2015 1 0046931

(51) Int. Cl.
*A61C 7/14* (2006.01)
*A61C 7/34* (2006.01)
(Continued)

(52) U.S. Cl.
CPC .................. *A61C 7/14* (2013.01); *A61C 7/22* (2013.01); *A61C 7/34* (2013.01); *A61C 7/125* (2013.01); *A61C 7/20* (2013.01); *A61C 7/287* (2013.01)

(58) Field of Classification Search
CPC .... A61C 7/14; A61C 7/12; A61C 7/34; A61C 7/20; A61C 7/287; A61C 7/143; A61C 7/148; A61C 7/22
See application file for complete search history.

(56) References Cited

U.S. PATENT DOCUMENTS

2009/0004619 A1* 1/2009 Oda ........................ A61C 7/14
433/24
2009/0117509 A1 5/2009 Minium
(Continued)

FOREIGN PATENT DOCUMENTS

CN 201040037 Y 3/2008
CN 101815478 8/2010
(Continued)

OTHER PUBLICATIONS

International Search Report for international application No. PCT/CN2016/072085, dated May 3, 2016 (4 pages, including English translation).

(Continued)

*Primary Examiner* — Heidi M Eide
(74) *Attorney, Agent, or Firm* — Hamre, Schumann, Mueller & Larson, P.C.

(57) ABSTRACT

The present disclosure discloses a traction bracket, an orthodontic system, and an orthodontic method thereof. The traction bracket includes a traction component, a main body, a cover body and a connecting component, wherein a surface of the main body is provided with a main groove, the main body is provided with a arrestment-traction hole, one end of the arrestment-traction hole is opened at a surface of the main body to form a traction hole, and another end of the arrestment-traction hole is opened at the main groove of the main body to form an arrestment hole, the traction component matches and is connected to the arrestment-traction hole, the main body is connected to the cover body via a connecting component, and the bottom surface of the cover body matches the surface of the main body and covers the main groove. The traction component of the traction bracket according to the present disclosure can be easily installed, and is equipped with bolt accessories in two specifications, i.e., a traction bolt and an arrestment bolt. The traction bolt can facilitate sliding of the bracket. When the traction bolt is replaced with an arrestment bolt, the movement of the bracket and the arch wire can be stopped, to strengthen anchorage, achieve removal of the clearance between the arch wire and the groove, and achieve the correction effect of accurate expression of the torque of the bracket.

8 Claims, 13 Drawing Sheets

(51) Int. Cl.
    *A61C 7/22*      (2006.01)
    *A61C 7/20*      (2006.01)
    *A61C 7/28*      (2006.01)
    *A61C 7/12*      (2006.01)

(56) References Cited

U.S. PATENT DOCUMENTS

| | | | |
|---|---|---|---|
| 2009/0325120 A1* | 12/2009 | Lewis | A61C 7/287 433/13 |
| 2011/0269093 A1 | 11/2011 | Waugh, Jr. | |
| 2012/0315595 A1* | 12/2012 | Beaudoin | A61C 7/287 433/9 |
| 2016/0128804 A1 | 5/2016 | Ji | |

FOREIGN PATENT DOCUMENTS

| | | |
|---|---|---|
| CN | 103385762 A | 11/2013 |
| CN | 203677274 U | 7/2014 |
| CN | 104055587 | 9/2014 |
| CN | 104138299 A | 11/2014 |
| CN | 204636585 | 9/2015 |
| WO | 2011040050 | 4/2011 |

OTHER PUBLICATIONS

First Office Action and Search Report issued for Chinese Patent Application No. 201510046931.X, dated Sep. 1 2017, 7 pages.

\* cited by examiner

TRACTION BRACKET, ORTHODONTIC SYSTEM AND ORTHODONTIC METHOD THEREFOR

FIELD

The present disclosure relates to orthodontic techniques and the field of teeth correction, in particular to a traction bracket, an orthodontic system, and an orthodontic method thereof.

BACKGROUND

A bracket, as an important component in orthodontic techniques, is an appliance used to correct irregularities of teeth. The bracket can be directly bonded to a dental crown surface through adhesive, and an arch wire applies various types of orthodontic forces to the teeth via the bracket to achieve the orthodontic purpose. At present, a bracket ligation wing, a main groove and a base plate that are used globally are all integrated, an orthodontic arch wire is secured in the main groove, and the teeth and the bracket, as a whole, slide along the arch wire. The traction hook of the existing bracket is generally welded to the main body of the bracket directly, and is thus irremovable. The protruding traction hook would easily scratch oral mucosa. Thus, in order to make the patient comfortable, the traction hook is mounted when needed, and removed when unneeded. Moreover, in the process of a clinical orthodontic treatment, the size of the square or rectangular arch wire as used would generally be smaller than that of the main groove of the bracket, and an angle of clearance between 10° and 24° would be generated between the arch wire and the wall of the main groove of the bracket such that the arch wire cannot fully express the torque angle of the main groove of the bracket.

SUMMARY

On the basis of the foregoing reasons, it is necessary to provide a traction bracket in which the traction component can be conveniently installed, movement of the bracket and the arch wire can be stopped after a traction bolt (an arrestment bolt) is replaced and corresponding correction effects can be achieved, in addition to capability of assisting in sliding of the bracket.

A traction bracket is provided, including:
a connecting component;
a cylindrical traction component; and
a main body having a surface and a bottom surface, wherein the surface of the main body has a main groove, the main body is provided with a arrestment-traction hole, one end of the arrestment-traction hole is opened at the surface of the main body to form a cylindrical traction hole, another end of the arrestment-traction hole is opened at the main groove of the main body to form an arrestment hole, and the traction component matches and is connected to the arrestment-traction hole; and
a cover body having a bottom surface and a surface, wherein the main body and the cover body are connected between one another via the connecting component, and the bottom surface of the cover body matches the surface of the main body and covers the main groove.

In one exemplary embodiment, the surface of the cover body and the surface of the main body match with each other and are in smooth and curved shapes.

In one exemplary embodiment, the arrestment-traction hole has a threaded inner wall, an inner diameter of the arrestment hole at an end of the arrestment-traction hole adjacent to the main groove is smaller than that of the traction hole at an end adjacent to the surface of the main body, the cylindrical traction component has a cylindrical traction bolt and a cylindrical arrestment bolt, the traction bolt and the arrestment bolt both have threaded outer walls, a diameter of the traction bolt matches an inner diameter of the arrestment hole, a diameter of the arrestment bolt matches an inner diameter of the traction hole, an end of the arrestment bolt is provided with an arrestment protuberance that is matingly embedded in the arrestment hole, so that the arrestment bolt matches the arrestment-traction hole.

In one exemplary embodiment, the main groove divides the surface of main body into a first end portion and a second end portion, the first end portion is provided with the arrestment-traction hole, the first end portion of the main body is more prominent than the second end portion, and the surface of the first end portion of the main body is in a smooth and curved shape; and
the bottom surface of the cover body matches the surface of the second end portion of the main body, and the surface of the cover body is in a smooth and curved shape, and matches the surface of the first end portion of the main body to assume a shape similar to an ellipsoid.

In one exemplary embodiment, the first end portion of the main body is provided with a first slot at a side facing the second end portion, an opening dimension of the first slot is smaller than an internal dimension of the first slot, the cover body is provided with a second slot at a side facing the first slot of the main body, and an opening dimension of the second slot is smaller than an internal dimension of the second slot; and
the connecting component has a first connecting side and a second connecting side, the first connecting side matches the first slot, and the second connecting side matches the second slot.

In one exemplary embodiment, the first slot has a semicircular cross section along a direction of the main groove, the second slot has a rectangular cross section along a direction of the main groove, and one edge of an opening of the second slot has a protruding edge extending in a direction towards another edge of the opening; and
the first connecting side of the connecting component is in a shape of a semicircular cylinder matching the first slot which has a semicircular cross section, the second connecting side is in an L shape matching the second slot, and the first connecting side is located at an end portion of the second connecting side.

In one exemplary embodiment, the arrestment-traction hole in the first end portion of the main body has a threaded inner wall, an end of the arrestment-traction hole adjacent to the main groove has an inner diameter consistent with an inner diameter of the traction hole at an end more adjacent to the surface of the main body, the cylindrical traction component has an arrestment bolt and a traction bolt, the arrestment bolt and the traction bolt have screw jointing portions, withstanding portions and bolt caps, both the screw jointing portions and the withstanding portions are in a columnar shape and have a circular radial cross section; an end of the screw jointing portion is connected to an end of the withstanding portion; the bolt cap is connected to another end of the withstanding portion; and an outer diameter of the bolt cap is larger than that of the withstanding portion; and an outer diameter of the screw jointing portion is smaller than that of the withstanding portion, the outer diameter of the screw jointing portion matches an inner diameter of the arrestment-traction hole, and the outer diameter of the withstanding portion is greater than the inner diameter of the arrestment-traction hole. The screw jointing portion of the traction bolt has a length smaller than or equal to a length of the arrestment hole, a front end of the screw jointing portion cannot be screwed into the main groove, the screw jointing portion of the arrestment bolt has a length larger than a length of the arrestment hole, and the front end of the screw jointing portion can be screwed into the main groove and fixedly connected to an arch wire in the main groove.

Another objective of the present disclosure is to provide an orthodontic system.

An orthodontic system includes an arch wire and an elastic member, and further includes at least two of the traction brackets, wherein the arch wire passes through the main groove in the surface of the main body, and is connected to the traction components on the two traction brackets via the elastic member.

A further objective of the present disclosure is to provide an orthodontic method.

An orthodontic method includes following steps:

securing, by bonding, a main body of a traction bracket of an orthodontic system to a surface of a tooth to be corrected, and passing an arch wire of the orthodontic system through a main groove of the traction bracket according to arrangement and configuration of a patient's teeth;

wherein when it is required to move a tooth, a traction component is inserted and secured into a arrestment-traction hole, and is connected to the traction components on other teeth via elastic members, the traction components of the traction brackets on the teeth to be corrected mesiodistally are fixedly connected via the elastic members, and teeth movement and correction are realized by a stretching function of a traction wire; and wherein when it is required to secure a tooth, a traction component is inserted into and passes through an arrestment hole and via a arrestment-traction hole, so that an end portion of the traction component and an arch wire in the main groove are closely connected to realize arrestment of the arch wire. The arrested and secured tooth serves as an anchorage, and movement of other traction brackets pulled by the traction components drives corresponding teeth to move and correct. After all the teeth have completed movement and the arch wire is in full contact with the inner wall of the main groove via an arrestment bolt, an angle of clearance between the arch wire and the main groove is removed, so that all the teeth are in a torque angle preset by the main groove.

With respect to the traction bracket according to the present disclosure, by cooperation among the main body, the cover body and the connecting component, the first end portion of the main body is provided with a arrestment-traction hole, one end of the arrestment-traction hole is opened at the surface of the main body, and another end of the arrestment-traction hole is opened in a direction of the main groove of the main body. The arrestment-traction hole is designed such that the traction brackets on the surface of two spaced apart or adjacent teeth can enable two traction components to be under stress when pulled and stretched by the traction wire. During application, one of the traction brackets is secured to the arch wire, and another traction bracket that needs to be adjusted on the tooth surface is not secured to the arch wire such that, by the action of the traction wire, the traction bracket that needs to be adjusted on the tooth surface is slowly pulled and stretched towards a direction of another traction bracket, thereby realizing adjustment in this direction.

With respect to the traction bracket involved in this disclosure, the arrestment-traction hole has a threaded inner wall, the inner diameter of the arrestment-traction hole at an end adjacent to the main groove is smaller than that at an end adjacent to the surface of the main body, the cylindrical traction component has a cylindrical traction bolt and a cylindrical arrestment bolt, the traction bolt and the arrestment bolt both have threaded outer walls, the traction bolt (a single-stage bolt) matches one end of the arrestment-traction hole adjacent to the arrestment hole, the diameter of one end of the arrestment bolt (a double-stage bolt) matches the inner diameter, which is relatively larger, of the arrestment-traction hole, and the diameter of another end of the arrestment bolt matches the inner diameter, which is relatively smaller, of the arrestment-traction hole, such that the arrestment bolt matches the arrestment-traction hole. After the traction bolt (the single-stage bolt) is screwed into the arrestment-traction hole, it can only function as a traction hook to assist in sliding of the bracket along the arch wire. On the other hand, after the arrestment bolt (the double-stage bolt) is screwed into the arrestment-traction hole, the tip of the bolt may enter the main groove of the bracket via the arrestment hole, and come into contact with the arch wire in the groove in a working state. The frictional force by screwing is so great that the arch wire cannot slide in the bracket, and the effect of movement stoppage is achieved.

With respect to the traction bracket according to the present disclosure, the main body, the cover body and the connecting component cooperate, in particular, the size of the main body along a direction of the main groove is larger than that of the main body perpendicular to the direction of the main groove in the transverse plane (a transverse direction), so that the traction bracket forms a shape similar to an ellipsoid along the direction of the main groove, or the size of the main body along the direction of the main groove is smaller than that in the plane (a transverse direction) of the main body perpendicular to the direction of the main groove, so that the traction bracket forms a shape similar to an ellipsoid along the direction of a short axis of the main groove (i.e., a direction perpendicular to the main groove). The surface of the cover body and the surface of the first end portion of the main body are matingly in a shape similar to an ellipsoid such that the length of the main groove is increased or decreased, the transverse diameter is increased or decreased, the length at which the bracket controls the arch wire is increased, and thus the control of an axis of a tooth is increased. Moreover, the design of the shape similar to an ellipsoid effectively reduces the height of the surface of the traction bracket, increases comfortability, and reduces uncomfortable feeling in the oral cavity of a patient during application.

With respect to the traction bracket according to the present disclosure, the first end portion of the main body is provided with a first slot at a side facing the second end portion, an opening dimension of the first slot is smaller than an internal dimension of the first slot, the cover body is provided with a second slot at a side facing the first slot of the main body, and an opening dimension of the second slot is smaller than an internal dimension of the second slot; and the connecting component has a first connecting side and a second connecting side, the first connecting side matches the first slot, and the second connecting side matches the second slot. By cooperation among the first slot, the second slot and the connecting component having the first connecting side and the second connecting side, the main body and the cover body can be firmly and fixedly connected. Installation and disassembly can be facilitated.

With respect to the traction bracket according to the present disclosure, the first slot has a semicircular cross section along a direction of the main groove, the second slot has a rectangular cross section along the direction of the main groove, and one edge of an opening of the second slot has a protruding edge extending in a direction towards another edge of the opening; the first connecting side of the connecting component matches the first slot, and the second connecting side is in an L shape matching the second slot. The two end portions are distinctly different in respect of the shape of the two slots. During installation, they can be easily installed in place by one installation, thus avoiding the occurrence of the phenomena such as misplacement of the connecting components.

With respect to the traction bracket according to the present disclosure, a T-shaped protruding portion is connected to the surface of the second end portion of the main body, a T-shaped slot portion is defined at a lateral side of the cover body facing the first end portion, the slot portion matches the protruding portion, and the protruding portion and the slot portion are designed such that cooperation between the cover body and the main body becomes closer, and the cover body will not easily move or fall off. During application, movement of the cover body and influence on a user's feeling are avoided.

With respect to the traction bracket involved in this disclosure, a ligation slot is designed to facilitate a ligation wire to be ligated in the ligation slot, which is more conducive to cooperation between the entire traction bracket and the arch wire. Protective wings are designed mainly to prevent the ligation wire ligated in the ligation slot from dislocation or displacement.

The orthodontic method according to the present disclosure can be easily implemented with less time and manual labor, and the equipment can be manufactured easily at a low cost. Moreover, the orthodontic method is relatively safe during application.

Figure 1:
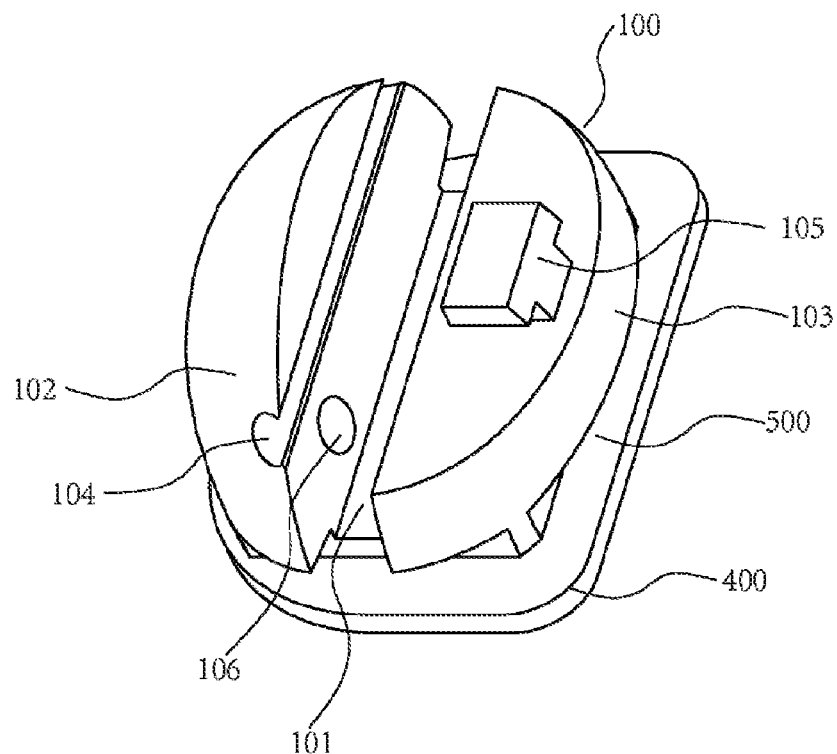
FIG. 1 is a front view of a main body and a base plate of a traction bracket according to an embodiment of the disclosure.
Figure 2:
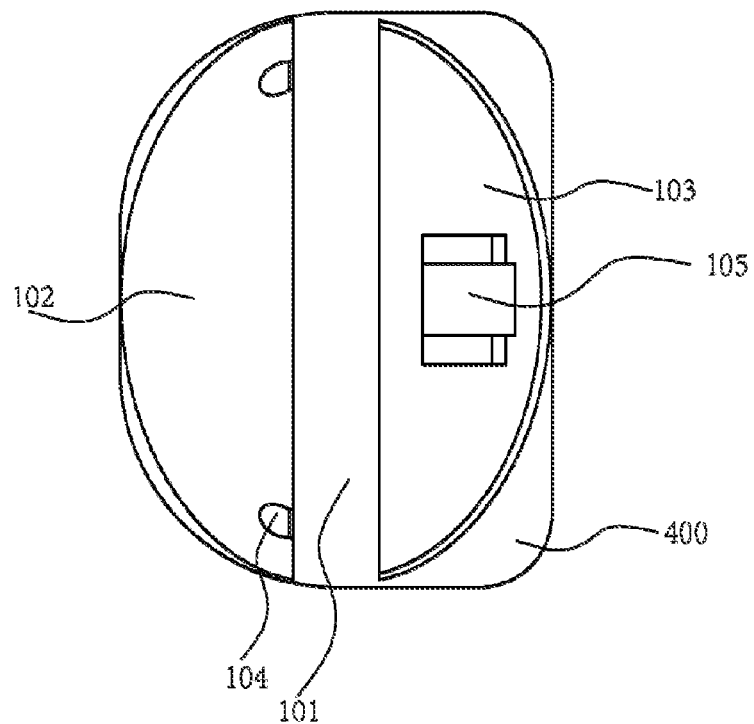
FIG. 2 is a top view of a main body and a base plate of a traction bracket according to an embodiment of the disclosure.
Figure 3:
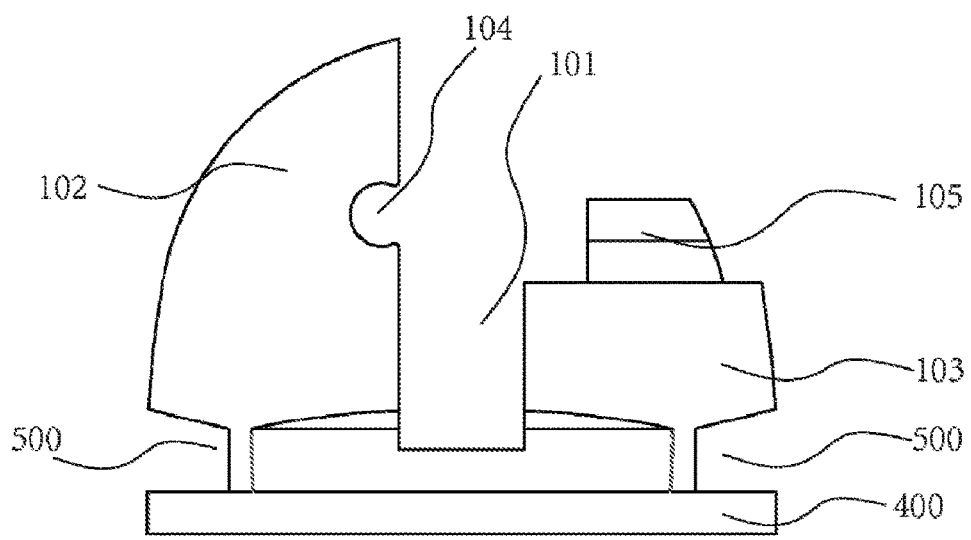
FIGS. 3-6 are side views of a main body and a base plate of a traction bracket according to an embodiment of the disclosure.
Figure 4:
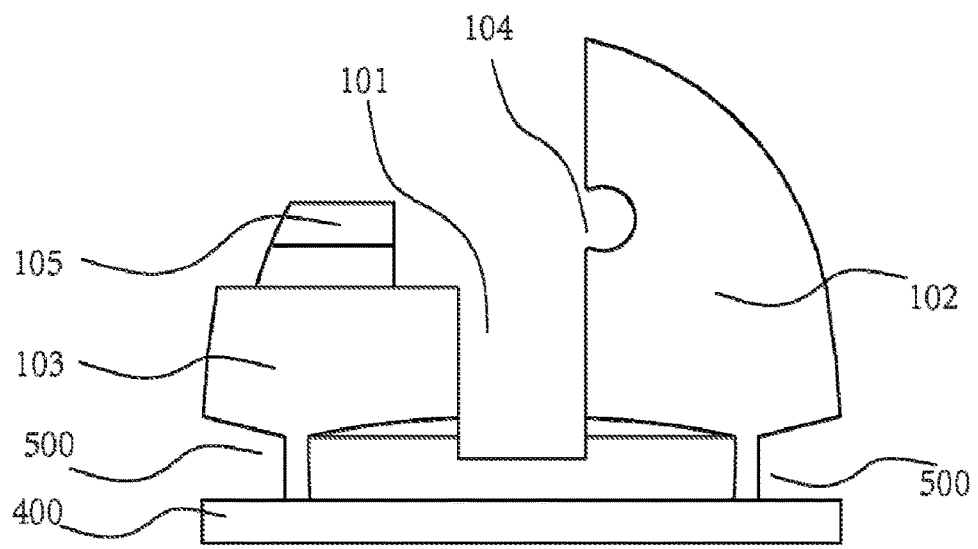
Figure 5:
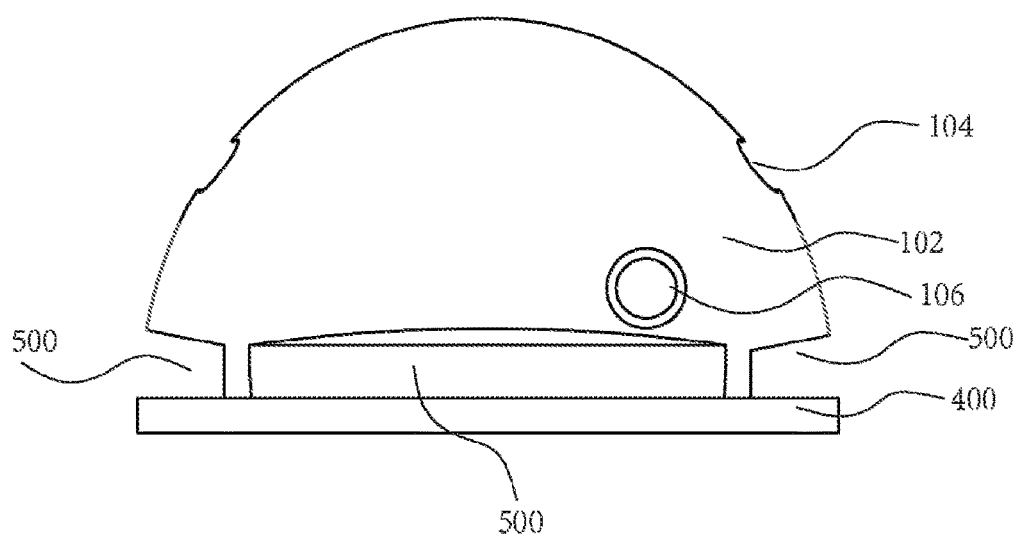
Figure 6:
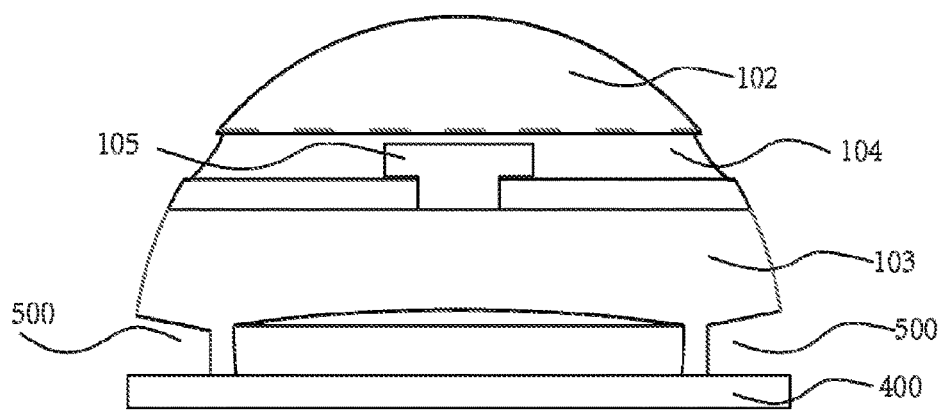
Figure 7:
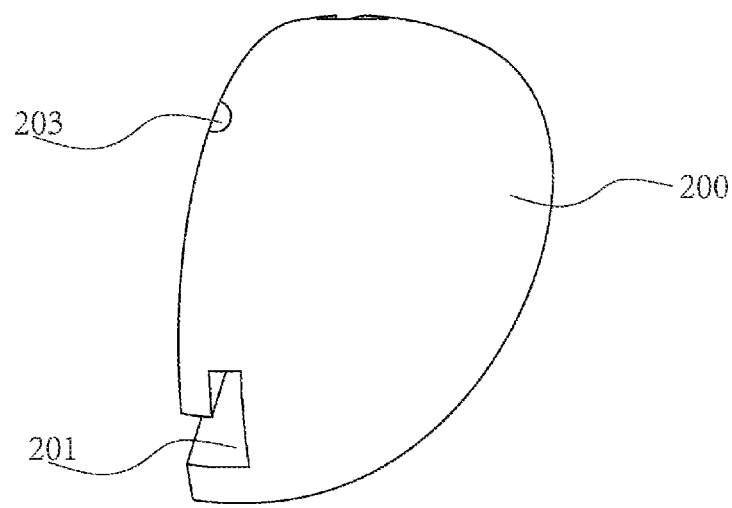
FIG. 7 is a front view of a cover body of a traction bracket according to an embodiment of the present disclosure.
Figure 8:
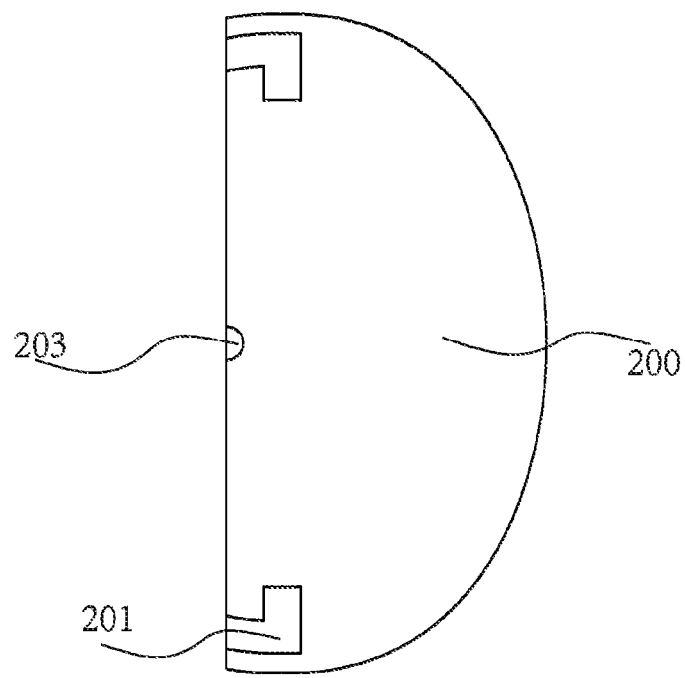
FIG. 8 is a top view of a cover body of a traction bracket according to an embodiment of the present disclosure.
Figure 9:
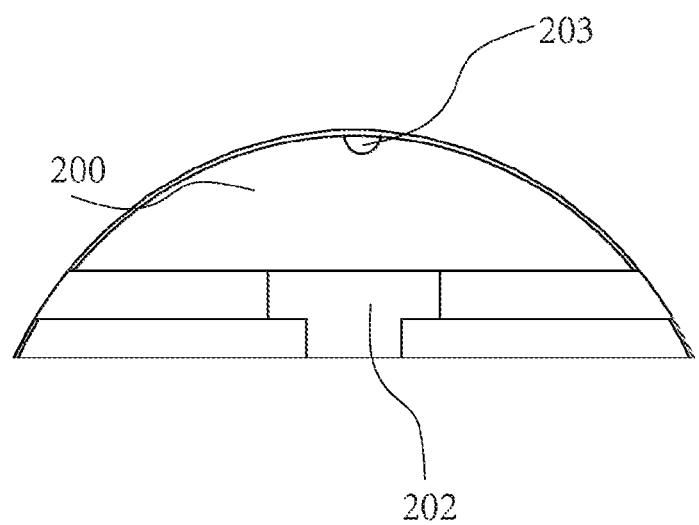
FIGS. 9 and 10 are side views of a cover body of a traction bracket according to an embodiment of the present disclosure.
Figure 10:
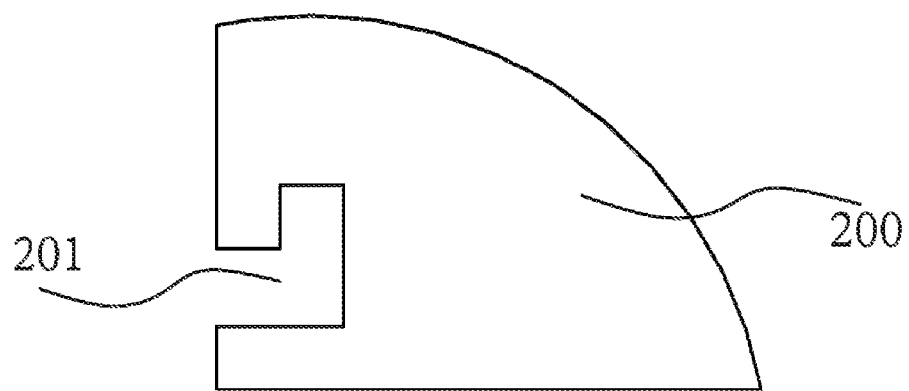

Denotations of the reference signs are provided below:

100 denotes a main body; 101 denotes a main groove; 102 denotes a first end portion; 103 denotes a second end portion; 104 denotes a first slot; 105 denotes a protruding portion; 106 denotes a arrestment-traction hole; 200 denotes a cover body; 201 denotes a second slot; 202 denotes a slot portion; 203 denotes a recessed portion; 300 denotes a connecting component; 301 denotes a first connecting side; 302 denotes a second connecting side; 400 denotes a base plate; 500 denotes a ligation slot; 600 denotes an arrestment bolt; 601 denotes a first fixation portion; 602 denotes a second fixation portion; 603 denotes a screw cap; 700 denotes a traction bolt; 800a denotes a traction bolt; 800b denotes an arrestment bolt; 801a and 801b denote screw jointing portions; 802a and 802b denote withstanding portions; 803a and 803b denote bolt caps; and 900 denotes an arch wire.

DETAILED DESCRIPTION OF THE PREFERRED EMBODIMENTS

The present invention will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "connected" or "coupled" to another element, it may be directly connected or coupled to the other element or intervening elements may be present. In contrast, when an element is referred to as being "directly connected" or "directly coupled" to another element, there are no intervening elements present.

Unless otherwise defined, all terms (including technical and scientific terms) used herein have the same meaning as commonly understood by one of ordinary skills in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. As used herein, the term "and/or" includes any and all combinations of one or more of the associated listed items.

An orthodontic system is provided in this embodiment, including an arch wire 900, an elastic member (a traction wire is used in this embodiment, which is not shown in the drawings), and a traction bracket.

Figure 13:
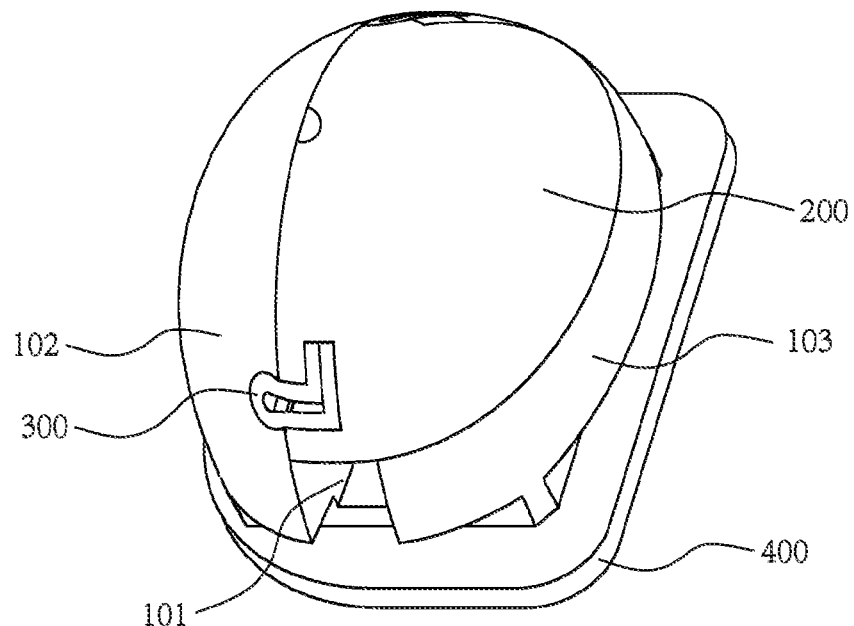
FIG. 13 is a front view of the traction bracket according to an embodiment of the present disclosure.
Figure 14:
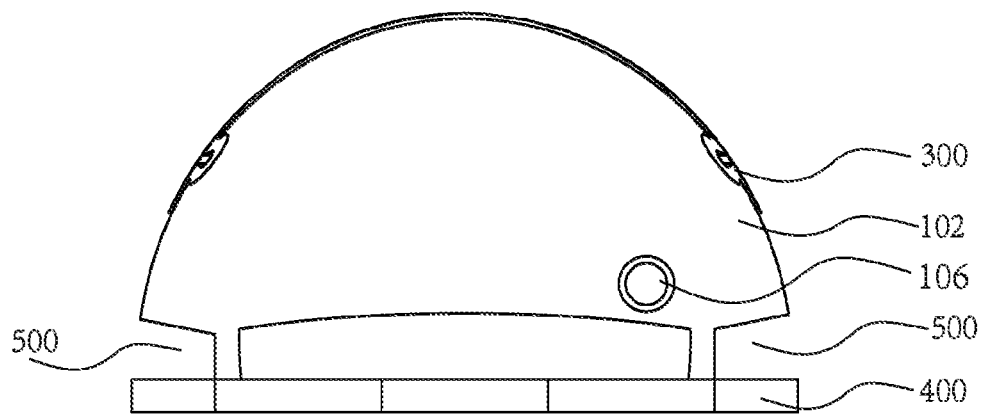
FIGS. 14 and 15 are side views of the traction bracket according to an embodiment of the present disclosure.
Figure 15:
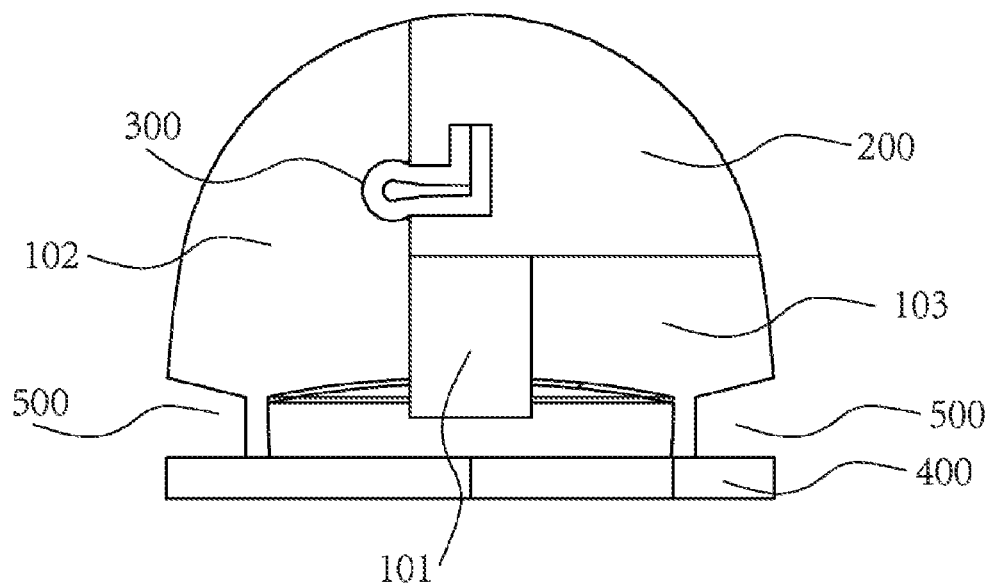

The traction bracket, as shown in FIGS. 13 to 15, includes a traction component, a main body 100, a cover body 200 and a connecting component 30. The traction component is cylindrical.

With reference to FIGS. 1 to 6, the main body 100 has a surface and a bottom surface, the surface of the main body 100 has a main groove 101, the main groove 101 divides the surface of main body 100 into a first end portion 102 and a second end portion 103, the size of the main body 100 along a direction of the main groove 101 is larger than that in the transverse plane of the main body perpendicular to the direction of the main groove 101, or the size of the main body 100 along the direction of the main groove 101 is smaller than that in the transverse plane of the main body perpendicular to the direction of the main groove 101, different sizes are designed for the size of the main body 100 along the direction of the main groove 101 according to different tooth widths, and the figure for this embodiment shows a traction bracket in one of the sizes. The first end portion 102 of the main body 100 is more prominent than the second end portion 103, and the surface of the first end portion 102 of the main body 100 is in a smooth and curved shape.

The main body is provided with a arrestment-traction hole 106 in the first end portion, one end of the arrestment-traction hole 106 is opened at a surface of the main body 100 to form an traction hole, and another end of the arrestment-traction hole 106 is opened at the main groove 101 of the main body 100 to form an arrestment hole.

Figure 16:
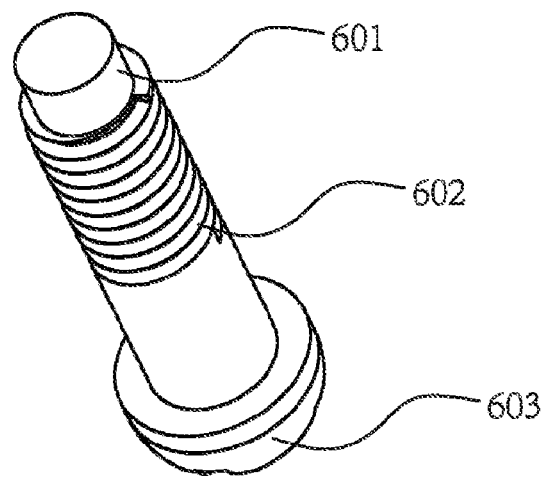
FIG. 16 is a front view of an arrestment bolt according to an embodiment of the present disclosure.
Figure 17:
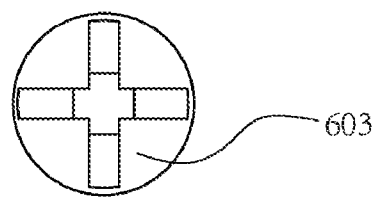
FIG. 17 is a top view of the arrestment bolt according to an embodiment of the present disclosure.
Figure 18:
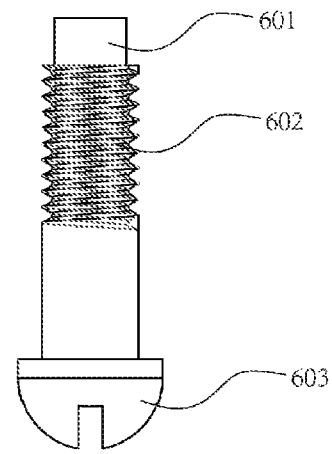
FIG. 18 is a side view of the arrestment bolt according to an embodiment of the present disclosure.

Further, with reference to FIGS. 16 to 18, the arrestment-traction hole 106 has a threaded inner wall, one end of the arrestment-traction hole 106 adjacent to the main groove 101 is provided with an arrestment hole, and another end of the arrestment-traction hole 106 adjacent to the surface of the main body 100 is provided with a traction hole. In the arrestment-traction hole 106, an inner diameter of the arrestment hole at an end adjacent to the main groove 101 is smaller than that of the traction hole at an end adjacent to the surface of the main body 100.

The cylindrical traction component has a cylindrical arrestment bolt 600, the arrestment bolt 600 matches the arrestment-traction hole 106, the traction bolt 700 and the arrestment bolt 600 both have threaded outer walls, a diameter of one end of the arrestment bolt 600 (a double-stage bolt) matches a larger inner diameter of the arrestment-traction hole 106, i.e., an inner diameter of the traction hole (an end with a larger inner diameter of the arrestment-traction hole), and a diameter of another end of the arrestment bolt 600 matches a smaller inner diameter of the arrestment-traction hole 106, so that the arrestment bolt 600 fully matches the arrestment-traction hole 106; in this embodiment, the arrestment bolt 600 includes a first fixation portion 601 in a cylindrical shape and a second fixation portion 602 in a cylindrical shape, the first fixation portion 601 is located at one end portion of the second fixation portion 602, another end of the second fixation portion 602 has a screw cap 603, the first fixation portion 601 is present as a cylindrical protrusion (i.e., an arrestment protuberance), the second fixation portion 602 has a threaded outer wall, and the diameter of the first fixation portion 601 (a protrusion) is smaller than that of the second fixation portion 602.

The diameter of the second fixation portion 602 of the arrestment bolt 600 matches an inner diameter of the arrestment-traction hole 106 at a side adjacent to the surface of the main body 100, and the diameter of the first fixation portion 601 matches an inner diameter of the arrestment-traction hole 106 at a side adjacent to the main groove 101. When the arrestment bolt 600 matches and is connected to the arrestment-traction hole 106, the second fixation portion 602 of the arrestment hole 600 is located at the side of the arrestment-traction hole 106 adjacent to the surface of the main body 100, and the first fixation portion 601 matches the arrestment-traction hole 106 at the side adjacent to the main groove 101. When the arrestment bolt 600 is fully and matingly connected to the arrestment-traction hole 106, the end portion of the second fixation portion 602 of the arrestment bolt 600 tightly abuts against a channel transitional position (i.e., a wall of which the aperture channel with a smaller inner diameter of the arrestment-traction hole 106 adjacent to the main groove 101 is more prominent than the aperture channel with a larger inner diameter of the arrestment-traction hole 106 at a side adjacent to the surface of the main body 100) with two different inner diameters inside the arrestment-traction hole 106, and the end portion of the first fixation portion 601 of the arrestment bolt 600 is more prominent than the side wall of the main groove 101.

Figure 19:
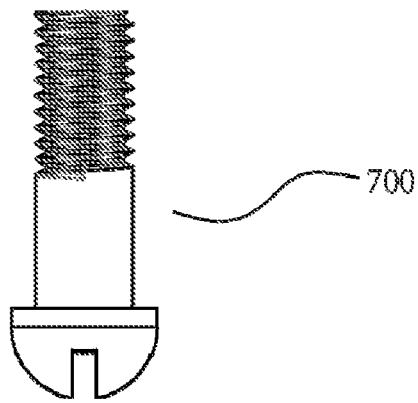
FIG. 19 is a side view of a traction bolt according to an embodiment of the present disclosure.
Figure 20:
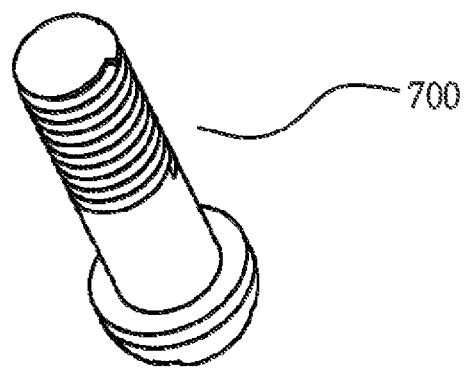
FIG. 20 is a front view of the traction bolt according to an embodiment of the present disclosure.

Further, with reference to FIGS. 19 to 20, the present embodiment further includes a traction bolt 700, and the diameter of the traction bolt 700 matches an inner diameter of the arrestment-traction hole 106 at a side adjacent to the surface of the main body 100, that is, the diameter of the traction bolt 700 (a single-stage bolt) is larger than the smaller inner diameter (the inner diameter of the arrestment-traction hole 106 at a side adjacent to the main groove 101) of the arrestment-traction hole 106. The traction bolt 700 matches the arrestment-traction hole 106. The traction bolt 700 is used as below: the traction bolt 700 passes through the arrestment-traction hole 106 of the main body 100 and is screwed into the main body 100 via an arrestment hole. Since the diameter of 700 is larger than the inner diameter of the arrestment-traction hole 106 at a side adjacent to the main groove 101, the end portion of the traction bolt 700 cannot be screwed into the main groove 101 and cannot come into contact with the arch wire 900 of the main groove. Thus, sliding of the arch wire 900 inside the main groove is not affected.

In this embodiment, the arrestment-traction hole 106 is present as a cylindrical aperture. The arrestment-traction hole 106 has a threaded inner wall. Meanwhile, the structures of the traction bolt 800a and the arrestment bolt 800b matching the arrestment-traction hole 106 are as follow.

Figure 24:
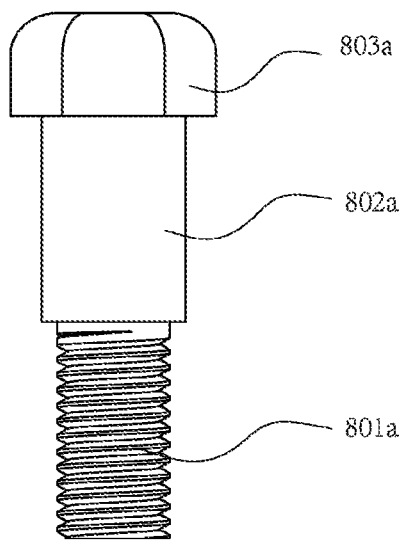
FIG. 24 is a schematic diagram of a traction bolt according to another embodiment of the present disclosure.
Figure 26:
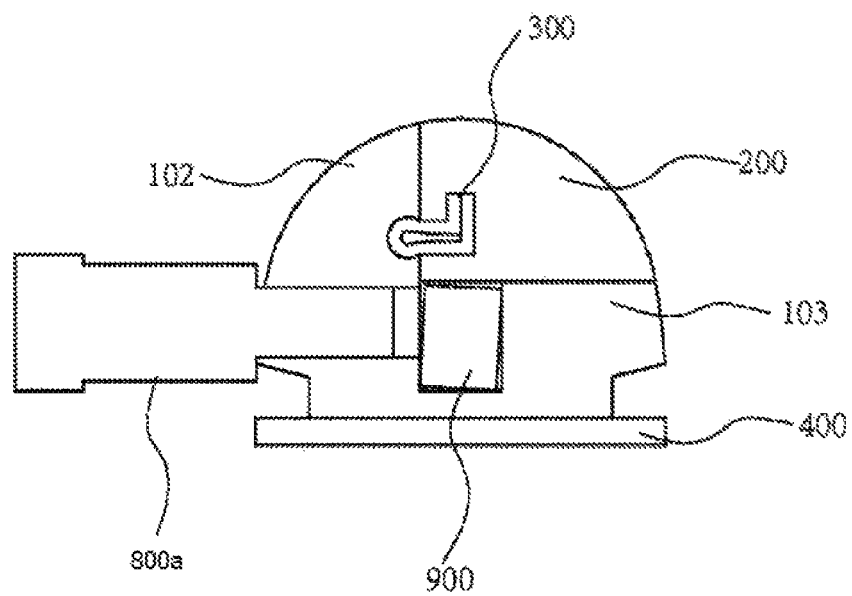
FIG. 26 is a side sectional view of the traction bracket and the traction bolt when cooperating according to an embodiment of the present disclosure.

Specifically, with reference to FIGS. 24 and 26, the traction bolt 800a: the traction bolt 800a has a screw jointing portion 801a, a withstanding portion 802a and a bolt cap 803a, both the screw jointing portion 801a and the withstanding portion 802a are present in a columnar shape, and both have circular radial cross sections. One end of the screw jointing portion 801a is connected to one end of the withstanding portion 802a. A central axis of the screw jointing portion 801a and that of the withstanding portion 802a are in the same straight line. The bolt cap 803a is connected to another end of the withstanding portion 802a. an outer diameter of the bolt cap 803a is larger than that of the withstanding portion 802a.

The outer diameter of the screw jointing portion 801a is smaller than that of the withstanding portion 802a. The outer diameter of the screw jointing portion 801a matches an inner diameter of the arrestment-traction hole 106. The outer diameter of the withstanding portion 802a is larger than the inner diameter of the arrestment-traction hole 106. The length of the screw jointing portion 801a is not larger than the length of the arrestment-traction hole 106. When the arrestment bolt 800a is inserted into the arrestment-traction hole 106, the screw jointing portion 801a is rotatably connected to the arrestment-traction hole 106. When the withstanding portion 802a abuts against the outer surface of the main body 100, the screw jointing portion 801a would not go beyond the arrestment-traction hole 106 and would not enter the main groove 101. The withstanding portion 802a of the traction bolt 800a can be used to hook the traction wire.

Figure 25:
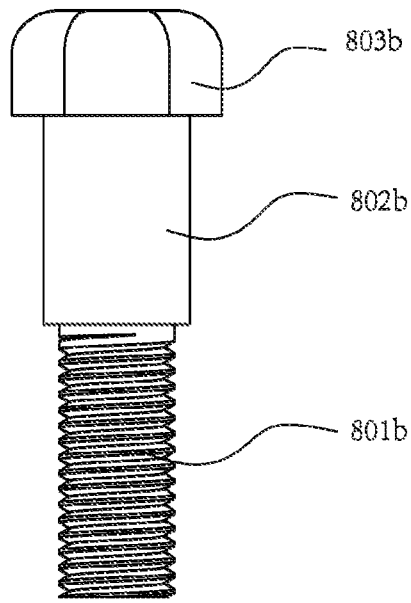
FIG. 25 is a schematic diagram of an arrestment bolt according to another embodiment of the present disclosure.
Figure 27:
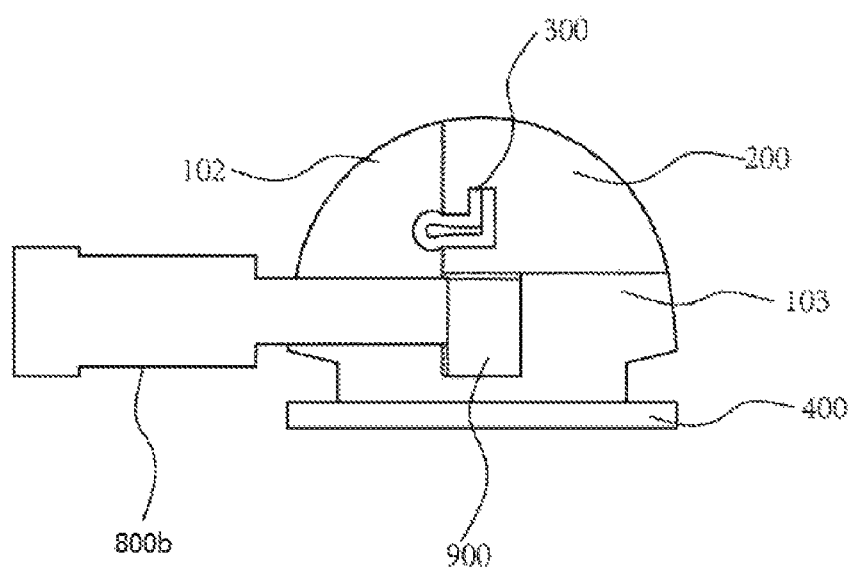
FIG. 27 is a side sectional view of the traction bracket and the arrestment bolt when cooperating according to an embodiment of the present disclosure.

With reference to FIGS. 25 and 27, the arrestment bolt 800b: the arrestment bolt 800b has a screw jointing portion 801b, a withstanding portion 802b and a bolt cap 803b, the screw jointing portion 801b and the withstanding portion 802b are both in a columnar shape, and both have circular radial cross sections. One end of the screw jointing portion 801b is connected to one end of the withstanding portion 802b. The central axis of the screw jointing portion 801b and that of the withstanding portion 802b are located in the same straight line. The bolt cap 803b is connected to another end of the withstanding portion 802b. an outer diameter of the bolt cap 803b is larger than that of the withstanding portion 802b.

The outer diameter of the screw jointing portion 801b is smaller than that of the withstanding portion 802b. The outer diameter of the screw jointing portion 801b matches an inner diameter of the arrestment-traction hole 106. The outer diameter of the withstanding portion 802b is larger than the inner diameter of the arrestment-traction hole 106. The length of the screw jointing portion 801b is larger than that of the arrestment-traction hole 106, but is smaller than the sum of the length of the arrestment-traction hole 106 and the width of the main groove 101. When the arrestment bolt 800b is inserted into the arrestment-traction hole 106, the screw jointing portion 801b is rotatably connected to the arrestment-traction hole 106. When the withstanding portion 802b abuts against the outer surface of the main body 100, the screw jointing portion 801b goes beyond the arrestment-traction hole 106 and goes into the main groove 101. The withstanding portion 802b of the arrestment bolt 800b can be used to hook the traction wire. In addition, the outer diameter of the screw jointing portion 801b may be equal to that of the withstanding portion 802b.

With reference to FIGS. 7 to 10, the cover body 200 has a bottom surface and a surface, the bottom surface of the cover body 200 matches the surface of the second end portion 103 of the main body 100, and the surface of the cover body 200 is in a smooth and curved shape and matches the surface of the first end portion 102 of the main body 100 to assume a shape similar to an ellipsoid.

The main body 100 and the cover body 200 are connected between one another via the connecting component 300.

During application, the arch wire 900 penetrates the main groove 101 of the surface of the main body 100.

The first end portion 102 of the main body 100 is provided with a first slot 104 at a side facing the second end portion 103, an opening dimension of the first slot 104 is smaller than an internal dimension of the first slot 104, and the first slot 104 has a semicircular cross section along the direction of the main groove 101.

The cover body 200 is provided with a second slot 201 at a side facing the first slot 104 of the main body 100, and an opening dimension of the second slot 201 is smaller than an internal dimension of the second slot 201.

Figure 11:
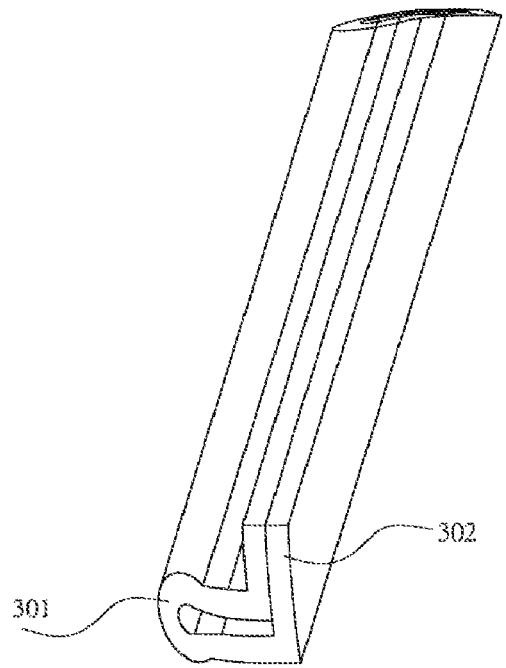
FIG. 11 is a front view of a connecting component of a traction bracket according to an embodiment of the present disclosure.
Figure 12:
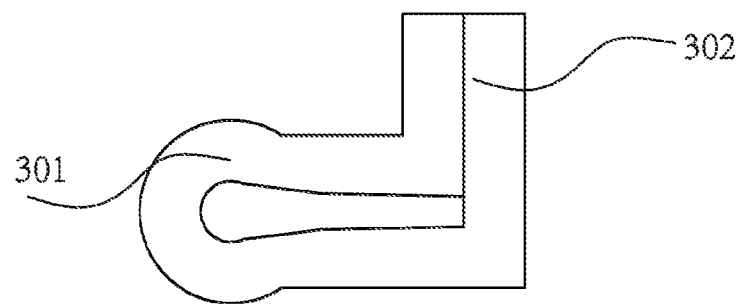
FIG. 12 is a side view of a connecting component of a traction bracket according to an embodiment of the present disclosure.

With reference to FIGS. 11 and 12, the connecting component 300 has a first connecting side 301 and a second connecting side 302, the first connecting side 301 matches the first slot 104, and the second connecting side 302 matches the second slot 201. The second slot 201 has a rectangular cross section along a direction of the main groove 101, and one edge of an opening of the second slot 201 has a protruding edge extending in a direction towards another edge of the opening; the first connecting side 301 of the connecting component 300 is in a shape of a semicircular cylinder matching the first slot 104 which has a semicircular cross section, the second connecting side 302 is in an L shape matching the second slot 201, and the first connecting side 301 is located at an end portion of the second connecting side 302.

A protruding portion 105 is connected at the surface of the second end portion 103 of the main body 100, the size of the top of the protruding portion 105 is larger than the size of the bottom thereof, and the top of the protruding portion 105 protrudes at both sides so that the protruding portion 105 is in a T shape; the cover body 200 is provided with a slot portion 202 at a side facing the first end portion 102, the slot portion 202 has an opening located at a side facing the first end portion 102 and an opening located at the bottom surface of the cover body 200, the opening at the side of the slot portion 202 facing the first end portion 102 is in a T shape, and the size of the opening located at the side of the slot portion 202 facing first end portion 102 matches the protruding portion 105.

Further, a base plate 400 is also included, the base plate 400 is connected to the bottom surface of the main body 100, and the base plate 400 has an adhesive layer at the bottom. The edge of the bottom surface, which is at a side facing the bottom plate 400, of the main body 100 has a recessed portion, and the recessed portion and the base plate 400 form ligation slots 500. There are at least two ligation slots 500, and each of the ligation slots 500 are uniformly distributed at the edge of the main body 100 at a side facing the base plate 400, and the outer edges of the recessed portion all have protrusions facing the base plate 400 to form protective wings.

Further, the edge of the top of the cover body 200 in this embodiment facing the main body 100 has a recessed portion 203 in a shape of a ¼ sphere to form a flip top opening, and the second recessed portion 203 matches the finger to open or close the cover body 200 and the main body 100.

The orthodontic system according to the present disclosure may be used in an orthodontic method including the following steps.

A set of traction brackets in different sizes (the sizes of the main body 100 along the direction of the main groove 101) may be selected according to arrangement and configuration of a patient's teeth and different tooth widths. The main bodies 100 of the traction brackets of an orthodontic system may be adhesively secured to the surface of the teeth to be corrected via the adhesive layers on the bottom of the base plates 400. The arch wire 900 of the orthodontic system may pass through the main grooves 101 on the main bodies 100 of the traction brackets, to enable the cover bodies 200 to match and cover the main bodies 100 of the traction brackets.

Figure 21:
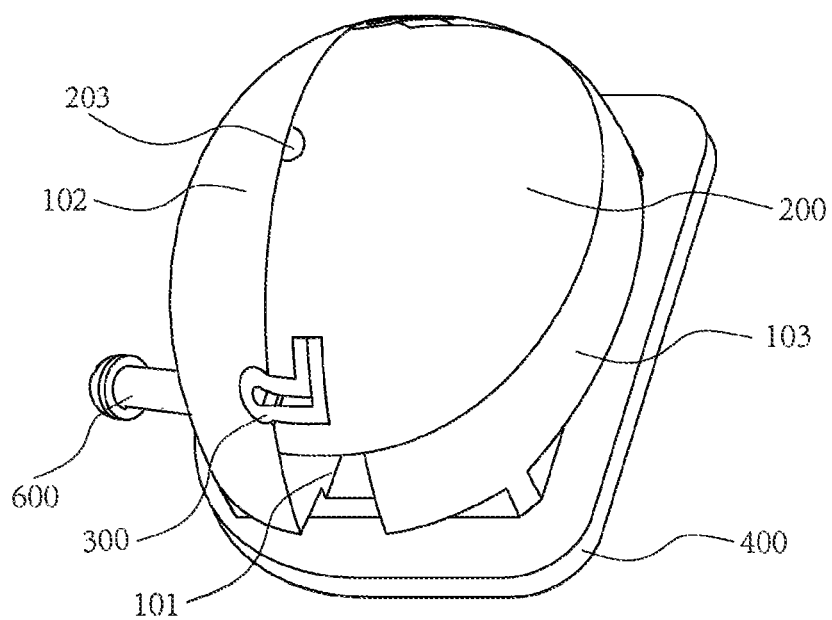
FIG. 21 is a front view of the traction bracket and the arrestment bolt when cooperating according to an embodiment of the present disclosure.
Figure 22:
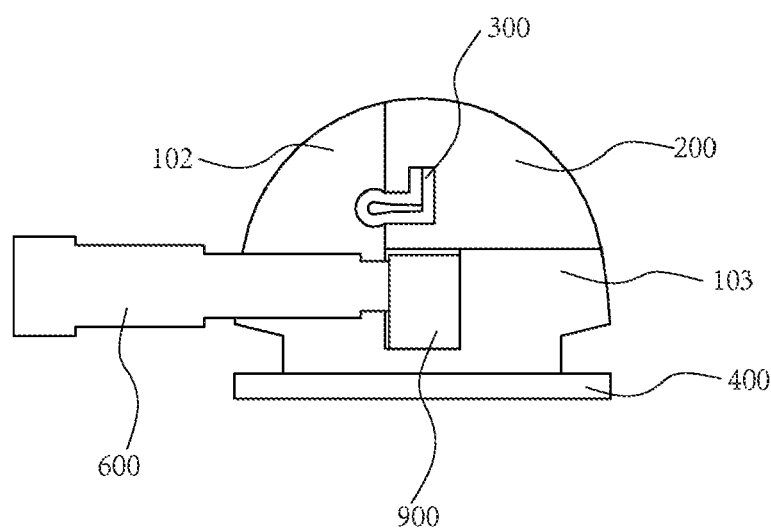
FIG. 22 is a side sectional view of the traction bracket and the arrestment bolt when cooperating according to an embodiment of the present disclosure.
Figure 23:
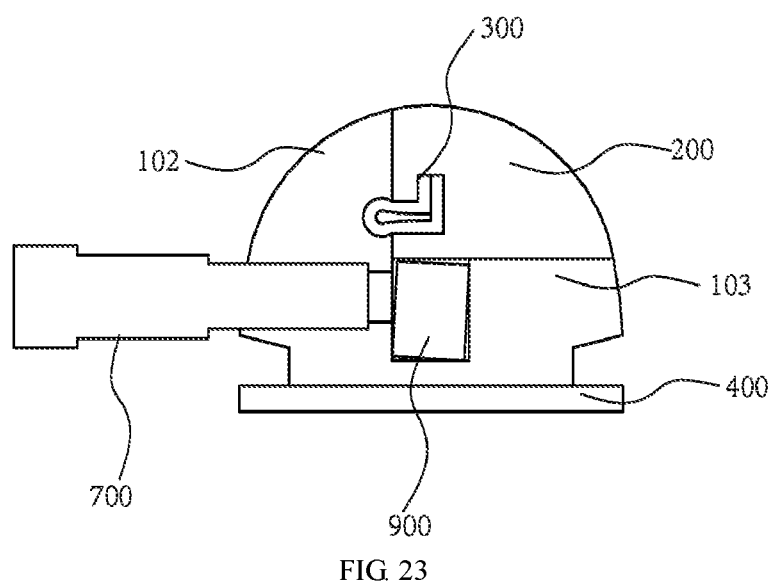
FIG. 23 is a side sectional view of the traction bracket and the traction bolt when cooperating according to an embodiment of the present disclosure.

When it is required to secure a tooth, i.e., when it is not required to move a certain tooth, the arrestment bolt 600 of the traction component is inserted into the arrestment hole through a arrestment-traction hole 106 (with reference to FIGS. 21, 22 and 23) and screwed tightly, so that the arrestment protuberance at the end portion of the arrestment bolt 600 of the traction component and the arch wire 900 in the main groove are closely connected to realize arrestment of the arch wire 900 by the arrestment protuberance and achieve the effect of securing the tooth. Meanwhile, the arrestment bolt 600 is used to bring the arch wire 900 into full contact with the inner wall of the main groove 101 of the bracket, an angle of clearance between the arch wire 900 and the main groove 101 is removed so that the torque angle preset by the main groove 101 can be fully expressed and root control of the teeth will be more accurate. The teeth corresponding to the arrested bracket would not generate movement with respect to the arch wire 900. Furthermore, the arrested teeth (i.e., the teeth that have been secured) may serve as fixation points, i.e., anchorages, to pull other teeth to move.

When it is required to move a certain tooth, a traction bolt 700 of a traction component is inserted and secured into a arrestment-traction hole. In such case, the traction bolt 700 cannot reach the arrestment hole, the traction bolt 700 on the tooth is connected to the traction bolts 700 of the traction components on other teeth via an elastic member (a traction wire), the traction components (traction bolts 700) of the traction bracket on the teeth that need to be corrected horizontally are fixedly connected via the elastic members (the traction wire), and teeth movement and correction are realized through the effect of the restoring force after the traction wire is stretched and deformed.

Where necessary, the arch wire 900 is secured in the ligation slot 500 of the traction bracket via a ligation wire so that the connection between the traction bracket and the arch wire 900 becomes firmer.

In the process of a clinical orthodontic treatment, the size of the square or rectangular arch wire 900 as used would be generally smaller than that of the main groove of the bracket, and the arch wire 900 would generate an angle of clearance between 10° and 24° with respect to the wall of the main groove in the bracket, such that the arch wire 900 cannot fully express the torque angle of the main groove in the bracket. Therefore, whilst the arrestment bolt in this embodiment is used, the front end of the arrestment bolt enters the main groove 101 to come into close contact with the arch wire 900 such that the arch wire 900 is in full contact with the wall of the main groove in the bracket. Accordingly, the angle of clearance between the arch wire 900 and the groove of the bracket can be entirely removed, so that the torque angle preset by the groove can be fully expressed and the root control of the teeth would be more accurate.

With respect to the traction bracket according to the present disclosure, by cooperation among the main body, the cover body and the connecting component, the main body is provided with a arrestment-traction hole in the first end portion, one end of the arrestment-traction hole is opened at the surface of the main body, and another end of the arrestment-traction hole is opened in a direction of the main groove of the main body. The arrestment-traction hole is designed such that the traction brackets on the surface of two spaced apart or adjacent teeth can allow two arrestment bolts to be under stress when pulled and stretched by the traction wire. During application, one of the traction brackets is secured to the arch wire, and another traction bracket on the surface of a tooth that needs to be adjusted is not secured to the arch wire such that, by the action of the traction wire, the traction bracket on the surface of the tooth that needs to be adjusted is slowly pulled and stretched towards a direction of another traction bracket, thereby realizing adjustment in this direction.

With respect to the traction bracket involved in this disclosure, the arrestment-traction hole has a threaded inner wall, an inner diameter of the arrestment-traction hole at an end adjacent to the main groove is smaller than that at an end adjacent to the surface of the main body, the cylindrical traction component has a cylindrical traction bolt and a cylindrical arrestment bolt, the traction bolt and the arrestment bolt both have threaded outer walls, the traction bolt (a single-stage bolt) matches an end of the arrestment-traction hole adjacent to the arrestment hole, the diameter of one end of the arrestment bolt (a double-stage bolt) matches the inner diameter, which is relatively larger, of the arrestment-traction hole, and the diameter of another end of the arrestment bolt matches the inner diameter, which is relatively smaller, of the arrestment-traction hole, so that the arrestment bolt matches the arrestment-traction hole. After the traction bolt (the single-stage bolt) is screwed into the arrestment-traction hole, it can only function as a traction hook to assist in sliding of the bracket along the arch wire. On the other hand, after the arrestment bolt (the double-stage bolt) is screwed into the arrestment-traction hole, the tip of the bolt may enter the main groove of the bracket via the arrestment hole, and come into contact with the arch wire in the groove in a working state. The frictional force by screwing is so great that the arch wire cannot slide in the bracket so as to achieve the effect of movement stoppage.

With respect to the traction bracket according to the present disclosure, the main body, the cover body and the connecting component cooperate, in particular, the size of the main body along a direction of the main groove is larger than that of the main body perpendicular to the direction of the main groove in a transverse plane (a transverse direction), so that the traction bracket forms a shape similar to an ellipsoid along the direction of the main groove, or the size of the main body along the direction of the main groove is smaller than that in the plane (a transverse direction) of the main body perpendicular to the direction of the main groove, so that the traction bracket forms a shape similar to an ellipsoid along the direction of a short axis of the main groove. The surface of the cover body and the surface of the first end portion of the main body are matingly in a shape similar to an ellipsoid such that the length of the main groove is increased or decreased, the transverse diameter is increased or decreased, the length at which the bracket controls the arch wire is increased, and thus the control of an axis of tooth is strengthened. Moreover, the design of the shape similar to an ellipsoid effectively reduces the height of the surface of the traction bracket and increases comfortability so as to reduce uncomfortable feeling in the oral cavity of a patient during application.

With respect to the traction bracket according to the present disclosure, the first end portion of the main body is provided with a first slot at a side facing the second end portion, an opening dimension of the first slot is smaller than an internal dimension of the first slot, the cover body is provided with a second slot at a side facing the first slot of the main body, and an opening dimension of the second slot is smaller than an internal dimension of the second slot; and the connecting component has a first connecting side and a second connecting side, the first connecting side matches the first slot, and the second connecting side matches the second slot. By cooperation among the first slot, the second slot and the connecting component having the first connecting side and the second connecting side, the main body and the cover body can be firmly and fixedly connected. Furthermore, installation and disassembly can be facilitated.

With respect to the traction bracket according to the present disclosure, the first slot has a semicircular cross section along a direction of the main groove, the second slot has a rectangular cross section along a direction of the main groove, and one edge of an opening of the second slot has a protruding edge extending in a direction towards another edge of the opening; the first connecting side of the connecting component matches the first slot, and the second connecting side is in an L shape matching the second slot. The two end portions are distinctly different in respect of the shape of the two slots. During installation, they can be easily installed in place by one installation, thus avoiding the occurrence of the phenomena such as misplacement of the connecting components.

With respect to the traction bracket according to the present disclosure, a T-shaped protruding portion is connected to the surface of the second end portion of the main body, a T-shaped slot portion is defined at a side of the cover body facing the first end portion, the slot portion matches the protruding portion, and the protruding portion and the slot portion are designed such that cooperation between the cover body and the main body becomes closer, and the cover body will not easily move or fall off. During application, movement of the cover body and influence on a user's feeling are avoided.

With respect to the traction bracket involved in this disclosure, a ligation slot is designed to facilitate a ligation wire to be ligated in the ligation slot, which is more conducive to cooperation between the entire traction bracket and the arch wire. Protective wings are designed mainly to prevent the ligation wire ligated in the ligation slot from dislocation or displacement.

With respect to the traction bracket involved in this disclosure, the main body further is provided with a arrestment-traction hole in the first end portion, one end of the arrestment-traction hole is opened at the surface of the first end portion of the main body, another end of the arrestment-traction hole is opened at a side of the first end portion of the main body facing the cover body. The arrestment-traction hole is designed such that removal of the traction bracket becomes more guaranteed. When the cover body cannot be normally separated from the main body, a force is exerted to insert a steel tube into the arrestment-traction hole, so that the cover body is under stress and thus separated from the main body.

As the size of square or rectangular arch wire as used would generally be smaller than that of the main groove of the bracket, and an angle of clearance between 10° and 24° would be generated between the arch wire and the main groove of the bracket, so that the arch wire cannot fully express the torque angle of the main groove of the bracket. Therefore, it is required to use the front end of the arrestment bolt to come into close contact with the main groove, so that the arch wire is in full contact with the wall of the main groove of the bracket. Accordingly, the angle of clearance between the arch wire and the groove of the bracket can be entirely removed so that the torque angle preset by the groove can be fully expressed and the root control of the teeth would be more accurate.

The traction component of the traction bracket according to the present disclosure can be easily installed. Apart from being capable of assisting in sliding of the bracket, the traction bolt (the arrestment bolt) may further be replaced to accomplish movement stoppage of the bracket and the arch wire, and achieve corresponding correction effects.

The orthodontic method according to the present disclosure can be easily implemented with less time and manual labor, and the equipment can be manufactured easily at a low cost. Moreover, the orthodontic method is relatively safe during application.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A traction bracket, comprising:
a connecting component;
a cylindrical traction component including a cap and a cylindrical body having a diameter smaller than a diameter of the cap;
a main body having a top surface, a bottom surface, a main groove, and an arrestment-traction hole, the main groove dividing the top surface into a first end portion having a first surface and a second end portion having a second surface, the arrestment-traction hole including a traction hole and an arrestment hole coaxial with the traction hole, the traction hole penetrating from the first surface of the main body to the arrestment hole and the arrestment hole penetrating from the traction hole to a side wall of the main groove, an inner diameter of the arrestment hole being smaller than an inner diameter of the traction hole, wherein the traction hole is configured to receive the cylindrical traction component, and the cylindrical traction component is matched and connected to the traction hole such that the cylindrical traction component protrudes from the first surface and the cap of the cylindrical traction component is spaced apart from the first surface; and
a cover body having a surface and a bottom surface, the main body and the cover body connected via the connecting component, and the bottom surface of the cover body matching the second surface of the main body and covering the main groove.

2. The traction bracket of claim 1, wherein the surface of the cover body and the second face of the main body match with each other and are in smooth and curved shapes.

3. The traction bracket of claim 1, wherein the arrestment-traction hole has a threaded inner wall, and
wherein the cylindrical traction component is selected from at least two types of bolts, the at least two types of bolts including a traction bolt or an arrestment bolt, the arrestment-traction hole having a configuration usable with both the traction bolt and the arrestment bolt, individually, and the traction bolt and the arrestment bolt each including a threaded portion with a threaded outer wall configured to engage the threaded inner wall of the arrestment-traction hole.

4. The traction bracket of claim 1, wherein the first end portion has a side wall that faces towards the second end portion, the side wall of the first end portion provided with a first slot, an opening dimension of the first slot being smaller than an internal dimension of the first slot,
  the cover body having a side wall configured to face towards the first slot of the main body, the side wall of the cover body is provided with a second slot, and an opening dimension of the second slot is smaller than an internal dimension of the second slot, and
  the connecting component has a first connecting side and a second connecting side, the first connecting side matches the first slot, and the second connecting side matches the second slot.

5. The traction bracket of claim 4, wherein the first slot has a semicircular cross section along a direction of the main groove, and the second slot has an L-shaped cross section along a direction of the main groove, and
  the first connecting side of the connecting component is in a shape of a semicircular cylinder matching the first slot which has a semicircular cross section, the second connecting side is in an L-shape matching the second slot, and the first connecting side is located at an end portion of the second connecting side.

6. An orthodontic system comprising:
an arch wire;
at least two of the traction brackets according to claim 1, wherein the arch wire passes through the main groove of the main body of each of the at least two traction brackets, and the arch wire is in contact with the cylindrical traction component of one of the at least two traction brackets.

7. An orthodontic method, comprising:
providing an orthodontic system according to claim 6,
securing, by bonding, the at least two of the traction brackets of the orthodontic system to teeth, the at least two traction brackets including a first traction bracket and a second traction bracket, the main body of the first traction bracket secured to a surface of a first tooth of the teeth, and the main body of the second traction body secured to a surface of a second tooth of the teeth;
passing the arch wire of the orthodontic system through the main groove of each of the traction brackets of the orthodontic system according to arrangement and configuration of the teeth; and
configuring the orthodontic system to correct a first tooth of the teeth, the first tooth being corrected by being moved from its current position or secured in said current position, and the orthodontic system has a first configuration for moving the first tooth and a second configuration for securing the first tooth,
wherein configuring the orthodontic system to the first configuration includes: inserting and securing the cylindrical traction component into the traction hole of the first traction bracket, and connecting the cylindrical traction component of the first traction bracket to at least the cylindrical traction component of the second traction bracket so that the first traction bracket is being pulled, wherein the pulling is configured to cause movement and correction of the first tooth, and
wherein configuring the orthodontic system to a second configuration includes: inserting the cylindrical traction component into and through the arrestment hole of the arrestment-traction hole of the first traction bracket so that an end portion of the cylindrical traction component contacts the arch wire in the main groove of the first traction bracket to cause arrestment of the arch wire and secure the first tooth, the secured first tooth anchoring the arch wire,
  wherein the orthodontic system pulls on at least the cylindrical traction component of the second traction bracket, the pulling causing movement and correction of the second tooth, and
wherein after all the teeth have completed movement and correction, the arch wire is configured to be in full contact with an inner wall of the main groove via the end portion of the cylindrical traction component in each of the traction brackets of the orthodontic system, and an angle of clearance between the arch wire and the main groove in each of the traction brackets of the orthodontic system is removed so that all the teeth are in a torque angle preset by the main groove.

8. A traction bracket, comprising:
a cylindrical traction component including a cap and a cylindrical body having a diameter smaller than a diameter of the cap;
a main body having a top surface, a bottom surface, a main groove, and an arrestment-traction hole, the main groove dividing the top surface into a first end portion having a first surface and a second end portion having a second surface, the arrestment-traction hole including a traction hole and an arrestment hole coaxial with the traction hole, the traction hole penetrating from the first surface of the main body to the arrestment hole and the arrestment hole penetrating from the traction hole to a side wall of the main groove, an inner diameter of the arrestment hole being equal to an inner diameter of the traction hole, wherein the traction hole is configured to receive the cylindrical traction component, and the cylindrical traction component is matched and connected to the traction hole such that the cylindrical traction component protrudes from the first surface and the cap of the cylindrical traction component is spaced apart from the first surface; and
a cover body having a surface and a bottom surface, the main body and the cover body connected via the connecting component, and the bottom surface of the cover body matching the second surface of the main body and covering the main groove
wherein the cylindrical traction component includes a threaded portion with a threaded outer wall configured to engage a threaded inner wall of the arrestment-traction hole,
wherein the cylindrical body of the cylindrical traction component includes a withstanding portion having a first end connected to the threaded portion and a second end connected to the cap,
wherein the cylindrical traction component is selected from at least two types of bolts, the at least two types of bolts including a traction bolt or an arrestment bolt, the arrestment-traction hole having a configuration usable with both the traction bolt and the arrestment bolt, individually,
  wherein the threaded portion of the traction bolt has a length that is less than or equal to a length of the arrestment-traction hole such that the threaded portion does not extend out of arrestment hole of the arrestment-traction hole into the main groove when the threaded portion of the traction bolt is fit into the arrestment-traction hole, and
  wherein the threaded portion of the arrestment bolt has a length that is greater than the length of the arrestment-traction hole so that the threaded portion of the arrestment bolt extends out of the arrestment-traction hole into the main groove when the arrestment bolt is fit into the arrestment-traction hole.

* * * * *